United States Patent
Plank

(10) Patent No.: US 6,695,614 B2
(45) Date of Patent: Feb. 24, 2004

(54) LIGHT BEAM HARDENING APPARATUS FOR CURING MATERIAL

(75) Inventor: Wolfgang Plank, Rankweil (AT)

(73) Assignee: Ivoclar Vivadent AG, Schaan (LI)

( * ) Notice: Subject to any disclaimer, the term of this patent is extended or adjusted under 35 U.S.C. 154(b) by 100 days.

(21) Appl. No.: 10/023,232

(22) Filed: Dec. 13, 2001

(65) Prior Publication Data

US 2002/0102513 A1 Aug. 1, 2002

Related U.S. Application Data

(60) Provisional application No. 60/276,346, filed on Mar. 16, 2001.

(30) Foreign Application Priority Data

Feb. 1, 2001 (DE) .......................................... 101 04 579

(51) Int. Cl.[7] ............................................... A61C 3/00
(52) U.S. Cl. .................................... 433/29; 250/504 H
(58) Field of Search ..................... 433/29; 250/504 H

(56) References Cited

U.S. PATENT DOCUMENTS

| | | | | |
|---|---|---|---|---|
| 5,420,768 A | * | 5/1995 | Kennedy | .................. 362/119 |
| 5,457,611 A | * | 10/1995 | Verderber | .................. 433/29 |
| 5,634,711 A | * | 6/1997 | Kennedy et al. | ............... 433/29 |
| 5,688,042 A | * | 11/1997 | Madadi et al. | ............... 362/240 |
| 6,220,722 B1 | * | 4/2001 | Begemann | ................... 362/231 |
| 6,331,111 B1 | * | 12/2001 | Cao | ............................. 433/29 |
| 6,439,888 B1 | * | 8/2002 | Boutoussov et al. | ........... 433/29 |
| 6,502,956 B1 | * | 1/2003 | Wu | ............................. 362/237 |

FOREIGN PATENT DOCUMENTS

DE          295 11 927 U1       2/1997

* cited by examiner

*Primary Examiner*—John J. Wilson
(74) *Attorney, Agent, or Firm*—John C. Thompson; Alan S. Korman

(57) ABSTRACT

A light beam hardening apparatus is provided for hardening a material, such as dental material, exposed to light emitted by the light beam hardening apparatus. The light beam hardening apparatus includes a semi-conductor light emitting source operable to emit light in the visible light spectral range of a light strength of at least 200 $mW/cm^2$, a base receptacle for supporting the semi-conductor light emitting source, and a heat conducting connection for conducting heat from the semi-conductor light emitting source to the base receptacle. The semi-conductor light emitting source includes a plurality of light emitting chips or light emitting diodes (LED). The base receptacle includes a plurality of cradles each for supporting therein a respective one of the light emitting chips.

14 Claims, 3 Drawing Sheets

LIGHT BEAM HARDENING APPARATUS FOR CURING MATERIAL

This claims the benefit of provisional application No. 60/276,346 filed Mar. 16, 2001.

BACKGROUND OF THE INVENTION

The present invention relates to a light beam hardening apparatus.

Light beam hardening apparatus for dental material hardening applications are today configured either as hand-held devices for the direct light polymerization of the dental material in the mouth of the dental patient or as stationary devices.

In particular with regard to hand-held devices, it is important that the polymerization be effected relatively rapidly and, at the least, at a rate which ensures a complete polymerization as well of larger teeth fillings comprised of light beam hardenable plastic.

The conventional light beam hardening apparatus is by far typically configured as a halogen bulb lamp having integrated reflectors whose light emissions are guided by a light guide rod, with the outlet end of the light guide rod being disposed immediately adjacent the filling to be hardened. The typical light beam hardenable dental plastic exhibits a spectral sensitivity whose maximum sensitivity lies in the region of visible light.

On the other hand, typical commercially available halogen bulb lamps emit visible light with substantially reduced ultraviolet (UV) portions of about 2%, for example. To improve the efficiency of the emitted light impact, it has been attempted to extend the spectral sensitivity of the plastic material which is to be polymerized into the long wavelength region. These attempts, however, have only succeeded in limited measure.

It has been further proposed to extend the emitted spectral region into the higher frequencies by means of filters, which only permit the passage therethrough of high wavelength light. This approach, however, requires that a substantial amount of light emitting energy be initially produced whereby, as a consequence thereof, the efficiency of this approach is correspondingly poor. At the same time, a cooling air flow must be regularly introduced which acts to limit the temperature of the light beam hardening apparatus and this air flow is not altogether pleasant for the dentist or the dental patient.

Moreover, it has long been known to deploy as light beam hardening apparatus semi-conductor light emitting sources which operate as light emitting diodes (LED). For example, German patent publication DE-GM 295 11 927 discloses a light beam hardening apparatus having a light emitting diode which emits light in the blue spectral region and which is powered by a battery or an accumulator.

It has been additionally proposed to deploy a plurality of LEDs for the power supply of a light guide rod. In this manner, the light output of the light beam hardening apparatus is improved. However, independent of whether the LEDs are configured and emit light as modules—that is, deployed in a common plastic housing—or as individual LEDs—that is, each deployed in its own respective plastic housing, the light output of LEDs is limited. The plastic housings are not only electrically insulating but they also suppress the shedding of heat so that a certain performance thickness of each of the light emitting chips cannot be exceeded due to the need to provide cooling of the plastic housings from the exterior.

It has, moreover, been proposed in other applications to adhesively secure light emitting chips on a metallic body. The heat resistance between the chip and the cooling body in such a configuration is, in fact, less than that of a configuration in which a chip is integrated into a plastic module. However, the adhesive layer acts as a heat blocker so that the danger exists here as well of an overheating of the chip or chips.

It has also long been a practice in the mounting of semi-conductors on cooling bodies to use a heat conducting paste. The heat conducting paste should displace a continuously insulating air layer which, due to the surface roughness of the outer surface, acts as a barrier to heat shedding. In spite of all efforts, however, the known light beam hardening apparatus with semi-conductor light emitting sources produce only a limited light output and are in this respect not especially suitable for dental applications.

OBJECTS AND SUMMARY OF THE INVENTION

The present invention offers a solution to the challenge of providing a light beam hardening apparatus which shortens the light hardening time so that a particularly strong heating up inside the mouth of the patient does not also occur due to the dental material hardening procedure.

In accordance with the present invention, it is particularly advantageous that, for the most part, cold light is used. A relatively reduced light strength is generated such that the long wavelength emission component is suppressed, whereby the intensity of the light beam radiation is higher in comparison to that of conventional devices.

The light beam hardening apparatus of the present invention unexpectedly generates a reduced temperature level in the mouth of the dental patient. As a first explanation for this, the intensive emissions shorten the handling time so that only a reduced heating up occurs in the area of the filling. However, a further explanation for this phenomenon lies in the fact that the temperature range of the light beam hardening apparatus is itself surprisingly markedly lower so that there is no particularly intensive heating from this source.

The heat from the light emissions from the chip are, in accordance with the present invention, immediately conducted away via heat conducting connections to a base receptacle of substantial size. This base receptacle is itself then heated up. However, the base receptacle can be very effectively cooled in that it can be configured with a substantially large outer surface. The base receptacle has, however, due to its mass, a particularly large heat capacity so that its temperature is raised by only a relatively modest amount in the event of a premature disposition of heat energy in the course of just a few seconds.

In an advantageous embodiment of the light beam hardening apparatus of the present invention, a so-called heat pipe is provided for conducting heat rearwardly away from the base receptacle. The thus rearwardly conducted heat can be in effect given off to the environment so that this embodiment can even be operated in a manner which does not require the blowing of cooling air onto the light beam hardening apparatus.

In another advantageous embodiment of the light beam hardening apparatus of the present invention, it is provided that each chip in the cradle is recessed relative to the outer surface of the cradle. This configuration results in a still further improved light emission efficiency. The cradle is preferably provided with an interior mirrored or reflective surface and operates as a micro reflector whereby the outer surfaces of the light emitting chips can be disposed in the focal burning point of the micro reflector. By virtue of this configuration, the light emitted toward the side is focused so that the loss of light caused by misdirected light emissions is markedly reduced.

In accordance with a further advantageous embodiment of the light beam hardening apparatus of the present invention, micro reflectors having integrated chips of the configuration just described are uniformly distributed over the outer surface of the base receptacle. The light emissions produced from this arrangement are bundled together in the front direction—that is, are emitted toward the location to be hardened by the light emissions—whereby the individual light emission bundles overlap and mix together.

In connection with such light emission bundling, it is also possible to provide various colors of the emission spectra of the individual chips and to undertake an individual control of each chip's emissions. For example, a focused red light can be emitted if, in a modified embodiment of the light beam hardening apparatus of the present invention, a heat handling procedure is to be performed.

It is particularly favorable, in one embodiment of the light beam hardening apparatus of the present invention, to use double connector wires. The especially light intensive chips of the light beam hardening apparatus of the present invention have high requirements for power, and the use of two gold or aluminum wires, each 30 $\mu$m, between the power supply conduit and the chip has shown itself as adequate for handling the power supply needs of the chips.

In another advantageous embodiment of the light beam hardening apparatus of the present invention, which is particularly suited for high performance chips, the so-called flip-chip technology can be implemented. In this connection, the contact is made to the underside of the chip and light emission is from the topside of the chip. The use of a bonded wire connection can be dispensed with in this embodiment as the contact can be accomplished, for example, by soldering.

In accordance with the present invention, the metallic heat conducting connection can be manufactured in any desired, suitable manner. For example, the base receptacle can also be manufactured with two coats and, in fact, with a metallic over coat and a ceramic base coat. Also, in accordance with the present invention, a substantially large heat capacity can be built in, especially if the metallic over coat completely covers the ceramic base coat and/or the silicon body, whereby the heat distribution is in this respect improved. Alternatively, an aluminum body can be used.

In a further advantageous embodiment of the light beam hardening apparatus of the present invention, it is provided that the base receptacle is generally configured in cup form and, in fact, is configured in a form which corresponds precisely to that of the receptacle or socket which has previously been used to support a halogen bulb lamp with reflectors. The receptacle or socket has cooling ribs along its outer surface and the base receptacle is preferably connected to the receptacle via heat conducting paste. An exchange during the life of the light beam hardening apparatus is as a rule generally not required as the LED chips have a very long operational life so that cost savings relative to light beam hardening apparatus with halogen bulb lamps are achieved due to reduced maintenance costs. It is particularly advantageous that the light beam hardening apparatus of the present invention eliminates the risk which is present in connection with halogen bulb lamps, that the breaking off of the polymerization procedure is caused by a burning through of the bulb lamp, thus resulting in a half hardened filling which must then be removed.

In a particularly advantageous embodiment of the light beam hardening apparatus of the present invention, it is provided that the emitted light beams are intensified onto a surface of limited cross sectional area by a prism body. The prism body is configured such that it shifts the individual light beam emissions in the outer region of the base receptacle emissions into the middle so that they can be guided practically without loss of light into the light guide rod. The prism body can additionally be enclosed within a cooling body having longitudinal cooling ribs on its exterior which facilitate the shedding of heat.

It is particularly advantageous, in one embodiment of the light beam hardening apparatus of the present invention, if the base receptacle including individual LED chips is substituted for a halogen bulb lamp having reflectors in a hand-held light hardening device. In this configuration, the exterior of the base receptacle is dimensioned so as to correspond with the dimensions of the inner surface of the receptacle, which receives the halogen bulb lamp. It is preferable if the exterior of the base receptacle is configured as a truncated cup and that connection pins are provided at those same locations as such connection pins are provided on halogen bulb lamps. The substitution of an appropriately dimensioned base receptacle of the light beam hardening apparatus of the present invention for a 50 W halogen bulb lamp offers a significantly improved emitted light performance for the same electrical power input. If the light beam hardening apparatus is controlled by a programmable controller, then, in the event that the base receptacle of the light beam hardening apparatus of the present invention has been substituted for a halogen bulb lamp with reflectors, the material hardening time will be correspondingly shortened to, for example, one-half the customary hardening time or even one-third the customary hardening time, which is a time saving benefit for the dentist.

DETAILED DESCRIPTION

Figure 1:
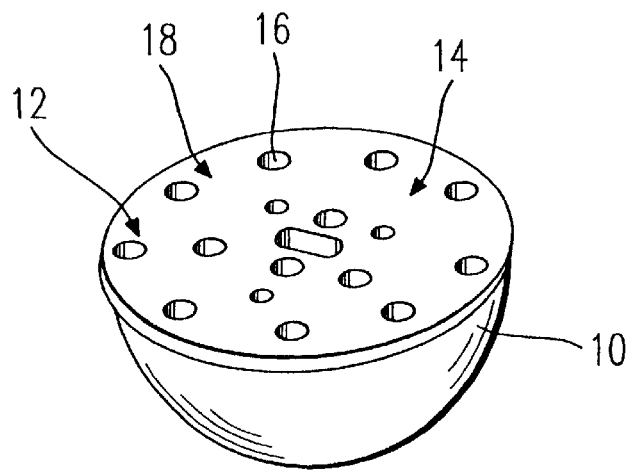
FIG. 1 is a perspective view of a base receptacle of an embodiment of the light beam hardening apparatus of the present invention.

In one embodiment of the light beam hardening apparatus of the present invention, the light beam hardening apparatus includes a base receptacle 10 having an outer surface 14 on which a plurality of semi-conductor light emitting sources 12 are disposed. The semi-conductor light emitting sources 12 are each individually mounted to the floor of a cradle 16 and are recessed with respect to the outer surface 18 of the cradle. As seen in the figures of the drawings showing the embodiment of the light beam hardening apparatus, a total of 12 semi-conductor light emitting sources 12 are provided which are uniformly distributed over the outer surface 14 of the base receptacle 10. Each of the semi-conductor light emitting sources 12 is soldered by silver solder to the cradle.

In accordance with the present invention, it is particularly advantageous if the light strength has a value of at least 200 mW/cm$^2$, and, especially, has a value of 300 mW/cm$^2$. It is especially beneficial if a blue or white semi-conductor light emitting source with a light strength of 1.000 or even 3.000 mcd is used. In accordance with the present invention, such light emitting diode (LED) chips produce a lightwave maximum whose wavelength corresponds to the maximum sensitivity of the typical dental material which is hardenable by light beam treatment. In this manner, an intensive light beam hardening is made available with only a decidedly small energy requirement.

The base receptacle 10 of the light beam hardening apparatus is comprised of an aluminum/magnesium alloy or composition such as AlMg3, which is applied to the outer surface by a galvanic silvering process. The depth of the silver coating is between 10 to 15 micrometers.

Figure 2:
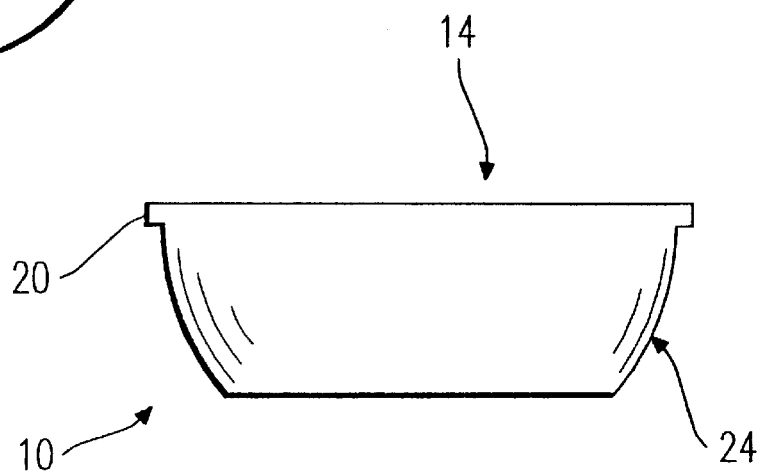
FIG. 2 is a side elevational view of the base receptacle shown in FIG. 1.

The depth of the solder coating for the manufacture of a metallic heat conducting connection is, in contrast to the depth of the silver coating, significantly greater comprising, for example, 100 micrometers. The surface 14 of the base receptacle 10—as can be seen in FIG. 2 from the point of view of the cradle 16—is planar. The base receptacle 10 is in the form of a truncated cone cup whereby a projecting edge 20 is provided for improved side support.

Figure 3:
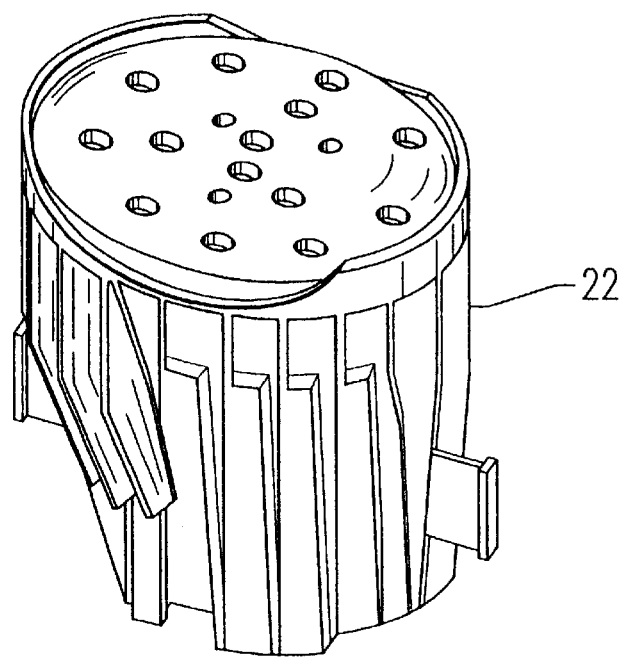
FIG. 3 is a plan view of the base receptacle shown in FIG. 1 in its seated disposition in a receptacle of the light beam hardening apparatus.

FIG. 3 shows one manner in which the base receptacle 10 can be received in a socket 22. The socket is provided with cooling fins or ridges along its outer surface and the inner surface of the socket preferably precisely corresponds with the outer surface 24 of the truncated cone cup of the base receptacle 10. The heat transfer between the base receptacle 10 and the cooled socket 22 can, as required, be improved by the use of a heat conducting paste.

Figure 4:
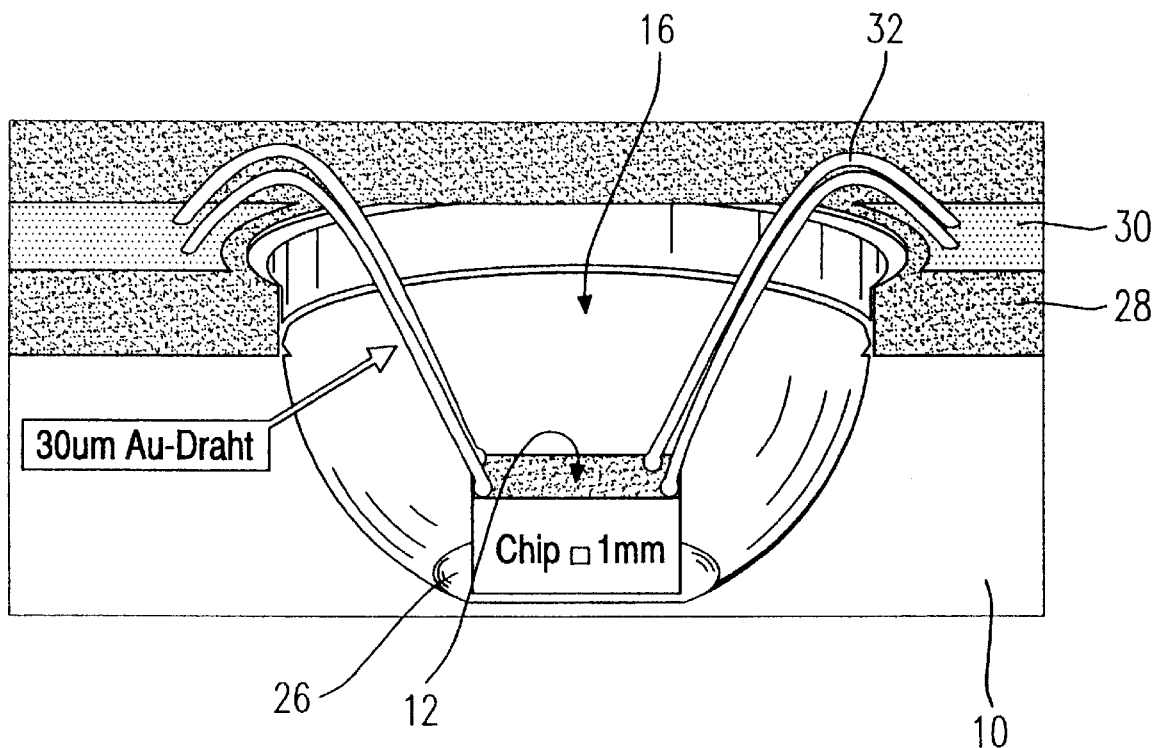
FIG. 4 is a sectional view of a cradle in the base receptacle shown in FIG. 1 and showing an individual semi-conductor light emitting source.

FIG. 4 shows the manner in which a chip or an individual semi-conductor light emitting source 12 can be received in a cradle 16. The cradle 16 is in the form of a reflector and the chip is arranged generally in the focal burning point of the reflector. The cradle includes a flat ground surface 26, which is dimensioned in correspondence with the dimension of the chip 12. The chip in its mounted location on the cradle is soldered to the cradle with a silver solder so that a metallic heat conducting connection exists between the chip and the base receptacle 10.

A conducting plate 28 is disposed on the outer surface of the base receptacle 10 adjacent each cradle 16 and each conducting plate 28 includes conducting leads 30, which serve as the current supply. Each chip is connected via a conventional coupling wire 32 with the conducting leads 30. In the illustrated embodiment of the light beam hardening apparatus, two coupling wires 32 are provided for each side in order to reduce a drop off in current and the ensuing drop off in power of the chip.

Figure 5:
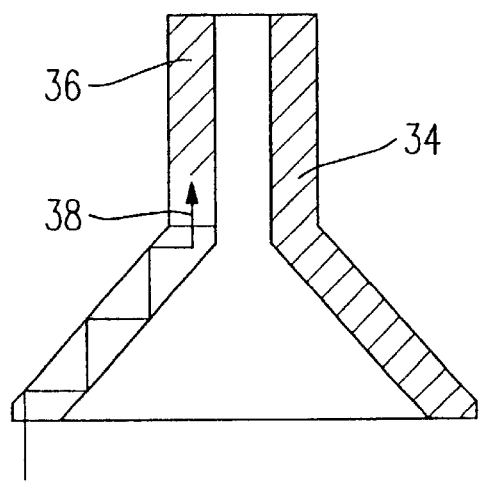
FIG. 5 is a sectional view of a prism body for handling light emissions of an embodiment of the light beam hardening apparatus of the present invention.

A prism body 34 can be seen in FIG. 5, which operates to collect the emitted lightwaves. The lightwaves, which are emitted by the chips that are disposed along the outer periphery of the base receptacle, are reflected several times in step wise manner by the prism body, whereby the thus multiple reflected light beams pass through a central area 36 and outlet members 38 of the prism body. The prism body acts to intensify the light beam emissions and to increase the lighting depth, and the prism body is connected to a light guide 40, as seen in FIG. 6.

Figure 6:
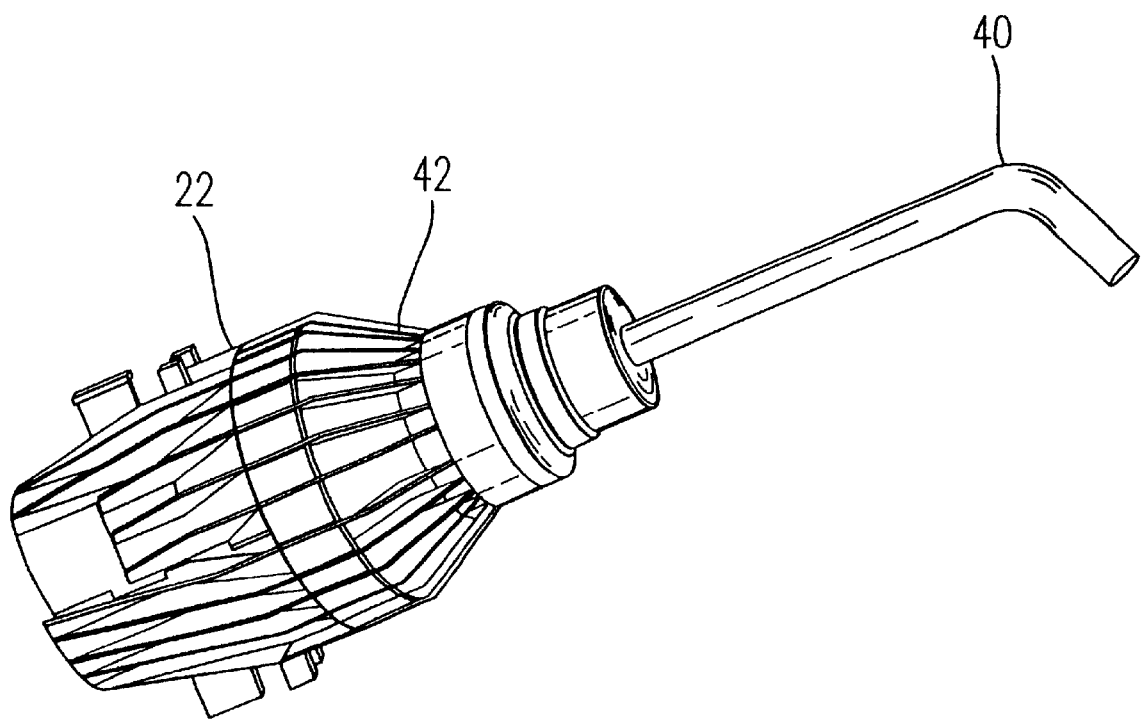
FIG. 6 is a perspective view of an embodiment of the light beam hardening apparatus of the present invention in its operationally assembled condition with its base receptacle, prism body, and a light beam guide.

As can be further seen in FIG. 6, the unit comprised of the base receptacle 10 and the prism body 34 is enclosed in a casing which is comprised of the socket 22 and an opposed socket 42. The two sockets 22 and 42 are each provided on their outer surfaces with longitudinally extending cooling fins or ribs, which facilitate the heat shedding capability of the socket. The heat shedding surface is enlarged through the metallic connection between the socket 22 and the opposed socket 42 and a continuous forced air stream can offer a particularly intensive cooling.

In a further advantageous configuration of the light beam hardening apparatus of the present invention, it is provided that the LEDs are deployed with differing intensity maxima. Thus, for example, LEDs with a peak of 440 nm and 470 nm are deployed. In this manner, it is possible to provide a capability for effecting the hardening of a wide range of dental materials since not every supplier of light hardenable dental material adjusts the dental material for treatment at a peak of 470 nm.

Measurements have shown that the light beam hardening apparatus of the present invention produces a light strength of about 600 mW/cm$^2$ as compared with a light strength of 1200 mW/cm$^2$ for a conventional light beam hardening apparatus; however, the use of the light beam hardening apparatus of the present invention achieves a higher relative intensity at lower light strengths.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims.

What is claimed is:

1. A light beam hardening apparatus for hardening a material exposed to light emitted by the light beam hardening apparatus, comprising:
    a semi-conductor light emitting source operable to emit light in the visible light spectral range of a light strength of at least 200 mW/cm$^2$, the semi-conductor light emitting source including a plurality of light emitting chips having a conductive substrate;
    a base receptacle for supporting the semi-conductor light emitting source base receptacle including a plurality of recessed cradles in the form of reflectors, each for supporting therein a respective one of the light emitting chips;
    a cooling body disposed adjacent the backside of the base receptacle, the cooling body having longitudinal ribs on its exterior for extracting heat therefrom; and
    a metallic heat conducting connection for each individual light emitting chip connecting the conductive substrate of each semi-conductor light emitting source to the base receptacle for conducting heat from the semi-conductor light emitting source to the base receptacle.

2. A light beam hardening apparatus according to claim 1, wherein the light emitting chips includes a plurality of light emitting diodes (LED) arranged such that the light emitted by at least one of the LEDs overlaps the light emitted by another LED.

3. A light beam hardening apparatus according to claim 1, wherein the semi-conductor light emitting chips are soldered to the base receptacle.

4. A light beam hardening apparatus according to claim 3, wherein each light emission source is soldered to the base receptacle by a silver solder layer having a thickness of between 20 and 500 μm.

5. A light beam hardening apparatus according to claim 1, wherein the base receptacle includes an outer surface comprised of at least one of metal and ceramic material.

6. A light beam hardening apparatus according to claim 1, wherein each cradle includes a silver reflective coating.

7. A light beam hardening apparatus according to claim 1, and further comprising a pair of power supply wires connected to each chip.

8. A light beam hardening apparatus according to claim 1, wherein the backside of the base receptacle and the cooling body is configured in a truncated cup shape generally corresponding to the shape of a reflector halogen bulb lamp.

9. A light beam hardening apparatus according to claim 1, and further comprising a light collecting device disposed relative to the semi-conductor light emitting source for collecting light emitted therefrom to focus the light through an outlet of the light collecting device having a cross section of less than 1 centimeter.

10. A light beam hardening apparatus according to claim 1, wherein the spectral region of the emitted light is at a maximum in the blue light region which includes ultraviolet light.

11. A light beam hardening apparatus according to claim 1, wherein the base receptacle includes a copper and silver alloy.

12. A light beam hardening apparatus according to claim 1, wherein the base receptacle is comprised of a ceramic material which has a metallic over coat.

13. A light beam hardening apparatus according to claim 1, wherein the light beam hardening apparatus is connectable to a power supply voltage of between 110 volts to 250 volts and includes a back up battery as an energy storage source.

14. A light beam hardening apparatus according to claim 1, wherein the base receptacle includes a pair of contact pins projecting from the backside of the base receptacle which are receivable in corresponding holes in a receptacle configured for normally receiving therein a reflector halogen bulb lamp.

* * * * *

UNITED STATES PATENT AND TRADEMARK OFFICE
CERTIFICATE OF CORRECTION

PATENT NO. : 6,695,614 B2
DATED : February 24, 2004
INVENTOR(S) : Wolfgang Plank It is certified that error appears in the above-identified patent and that said Letters Patent is hereby corrected as shown below:

Column 6,
Line 48, -- , the -- should be inserted after "source".

Signed and Sealed this

Fourth Day of May, 2004

JON W. DUDAS
*Acting Director of the United States Patent and Trademark Office*